US012646175B2

(12) United States Patent
Pappu et al.

(10) Patent No.: US 12,646,175 B2
(45) Date of Patent: Jun. 2, 2026

(54) MULTIVARIABLE ARTIFICIAL INTELLIGENCE (AI) BASED MONITORING SYSTEM FOR EARLY DETECTION OF GLAUCOMA

(71) Applicants: Geetha Pavani Pappu, Nabarangpur (IN); Birendra Biswal, Visakhapatnam (IN); Bhaskara Rao Jammu, Visakhapatnam (IN); Durga Srinivas Pindi, Visakhapatnam (IN); Raveendra Tammineni, Visakhapatnam (IN); Nasrin, Visakhapatnam (IN); Venkata Satya Sairam Metta, Visakhapatnam (IN); Bala Subrahmanyam Nemani, Visakhapatnam (IN)

(72) Inventors: Geetha Pavani Pappu, Nabarangpur (IN); Birendra Biswal, Visakhapatnam (IN); Bhaskara Rao Jammu, Visakhapatnam (IN); Durga Srinivas Pindi, Visakhapatnam (IN); Raveendra Tammineni, Visakhapatnam (IN); Nasrin, Visakhapatnam (IN); Venkata Satya Sairam Metta, Visakhapatnam (IN); Bala Subrahmanyam Nemani, Visakhapatnam (IN)

(73) Assignee: Sankar Foundation, Visakhapatnam (IN)

( * ) Notice: Subject to any disclaimer, the term of this patent is extended or adjusted under 35 U.S.C. 154(b) by 0 days.

(21) Appl. No.: 18/161,042

(22) Filed: Jan. 28, 2023

(65) Prior Publication Data
US 2025/0139778 A1 May 1, 2025

(51) Int. Cl.
*G06T 7/00* (2017.01)
*A61B 3/00* (2006.01)
(Continued)

(52) U.S. Cl.
CPC .......... *G06T 7/0014* (2013.01); *A61B 3/0025* (2013.01); *A61B 3/12* (2013.01);
(Continued)

(58) Field of Classification Search
CPC .... G06T 3/40; G06T 5/70; G06T 5/90; G06T 7/0014; G06T 7/11; G06T 7/13;
(Continued)

(56) References Cited

U.S. PATENT DOCUMENTS

2017/0270671 A1* 9/2017 Garnavi .................. G06T 7/187
2020/0401841 A1* 12/2020 Lee ....................... G06V 10/764
(Continued)

FOREIGN PATENT DOCUMENTS

CN 111667490 A * 9/2020 ........... G06K 9/3233
CN 114724231 A 7/2022
(Continued)

OTHER PUBLICATIONS

Yin et al."Automated segmentation of optic disc and optic cup in fundus images for glaucoma diagnosis," 2012 25th IEEE International Symposium on Computer-Based Medical Systems (CBMS), Rome, Italy, 2012, pp. 1-6, accessed May 5, 2025 via <https://ieeexplore.ieee.org/document/6266344> (Year: 2012).*
(Continued)

*Primary Examiner* — John Villecco
*Assistant Examiner* — Joshua B. Crockett
(74) *Attorney, Agent, or Firm* — Novel Patent Services LLC

(57) ABSTRACT

A multivariable artificial intelligence-based monitoring system for early detection of glaucoma and method thereof. The multivariable artificial intelligence system comprises a computing device having a control unit and one or more non-transitory storage devices for storing instructions to be executed by the control unit. The computing device is in
(Continued)

communication with an application server via a network. The computing device includes an input module, an image enhancing module, a feature extraction module, a post image processing module, and a parameter selection module. The proposed multivariable artificial intelligence system provides a deep learning architecture to segment the optic disc and optic cup in two ways using two different networks termed multi spatial attention feature fusion network (MSAFF-Net) and multi dilated edge extraction network (MDEE-Net) respectively.

13 Claims, 3 Drawing Sheets

(51) Int. Cl.

| | |
|---|---|
| *A61B 3/12* | (2006.01) |
| *G06T 3/40* | (2024.01) |
| *G06T 5/70* | (2024.01) |
| *G06T 5/90* | (2024.01) |
| *G06T 7/11* | (2017.01) |
| *G06T 7/13* | (2017.01) |
| *G06T 7/62* | (2017.01) |

(52) U.S. Cl.
CPC .................. *G06T 3/40* (2013.01); *G06T 5/70* (2024.01); *G06T 5/90* (2024.01); *G06T 7/11* (2017.01); *G06T 7/13* (2017.01); *G06T 7/62* (2017.01); *G06T 2207/20016* (2013.01); *G06T 2207/20081* (2013.01); *G06T 2207/20084* (2013.01); *G06T 2207/30041* (2013.01)

(58) Field of Classification Search
CPC ............. G06T 7/62; G06T 2207/20016; G06T 2207/20081; G06T 2207/2008; G06T 2207/30041; A61B 3/0025; A61B 3/12
See application file for complete search history.

(56) References Cited

U.S. PATENT DOCUMENTS

| | | | | |
|---|---|---|---|---|
| 2022/0121902 | A1* | 4/2022 | Hann | ........................ G06N 3/08 |
| 2022/0164947 | A1* | 5/2022 | Yu | ........................... G06T 7/0012 |
| 2023/0066166 | A1* | 3/2023 | Huang | ..................... A61B 3/12 |

FOREIGN PATENT DOCUMENTS

| | | | |
|---|---|---|---|
| CN | 115018756 A | | 9/2022 |
| IN | 201641025755 A | * | 11/2017 |

OTHER PUBLICATIONS

Bock et al. "Glaucoma risk index: Automated glaucoma detection from color fundus images", Med. Image Anal, V. 14, Iss. 3, 2010, p. 471-481, accessed May 5, 2025 via <https://www.sciencedirect.com/science/article/pii/S1361841509001509> (Year: 2010).*

"Hardware description language," Wikipedia, Jan. 20, 2023, accessed May 5, 2023 via <https://web.archive.org/web/20230120103626/https://en.wikipedia.org/wiki/Hardware_description_language> (Year: 2023).*

* cited by examiner

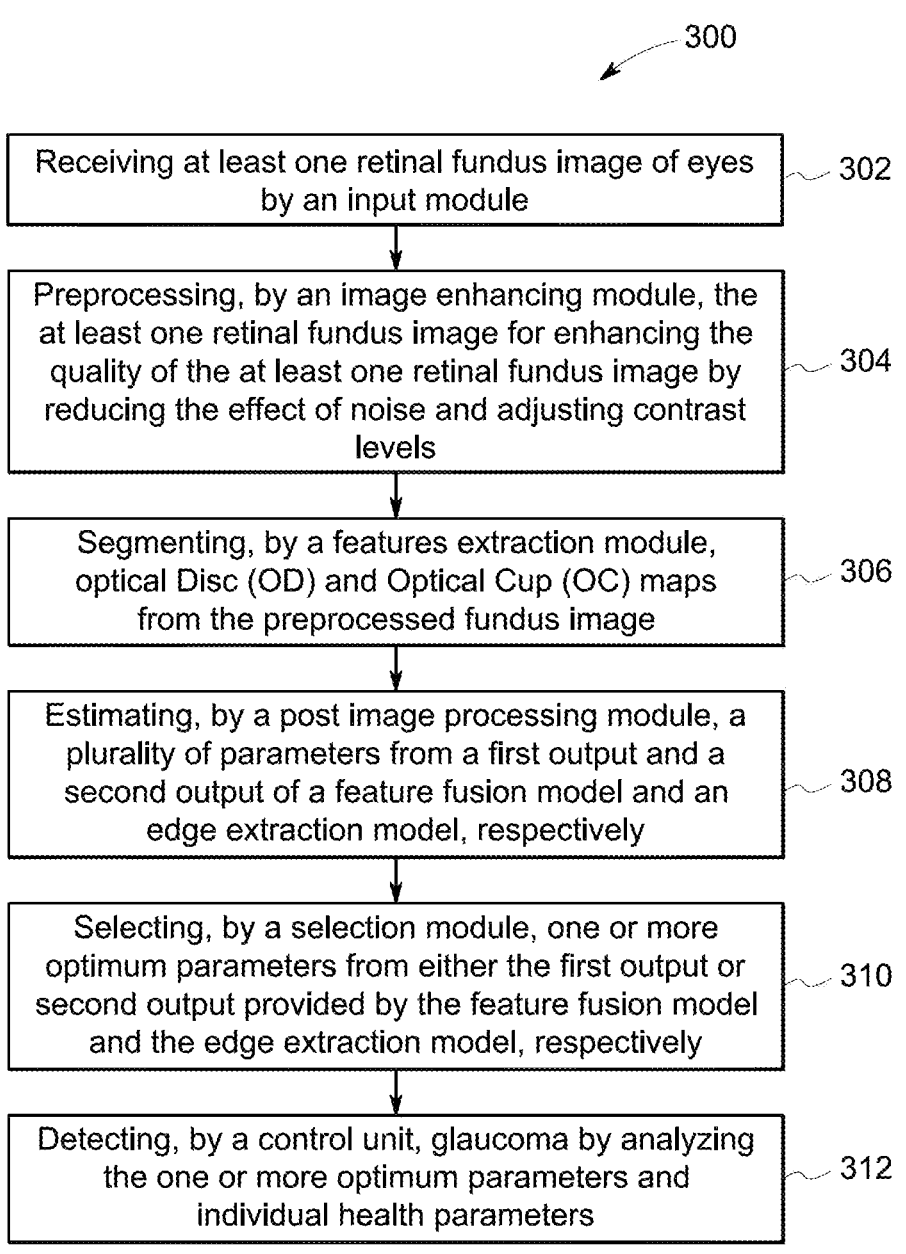

300

Receiving at least one retinal fundus image of eyes by an input module ~ 302

Preprocessing, by an image enhancing module, the at least one retinal fundus image for enhancing the quality of the at least one retinal fundus image by reducing the effect of noise and adjusting contrast levels ~ 304

Segmenting, by a features extraction module, optical Disc (OD) and Optical Cup (OC) maps from the preprocessed fundus image ~ 306

Estimating, by a post image processing module, a plurality of parameters from a first output and a second output of a feature fusion model and an edge extraction model, respectively ~ 308

Selecting, by a selection module, one or more optimum parameters from either the first output or second output provided by the feature fusion model and the edge extraction model, respectively ~ 310

Detecting, by a control unit, glaucoma by analyzing the one or more optimum parameters and individual health parameters ~ 312

FIG. 3

MULTIVARIABLE ARTIFICIAL INTELLIGENCE (AI) BASED MONITORING SYSTEM FOR EARLY DETECTION OF GLAUCOMA

BACKGROUND OF THE INVENTION

Technical Field

The present disclosure mainly relates to an image processing technique that extract information for the detection of glaucoma, and more specifically to a multivariable artificial intelligence guided monitoring system for early detection of glaucoma to predict and estimate the risk score of glaucoma.

Description of the Related Art

The retina is the light-sensitive tissue that senses light and sends images to the brain. Glaucoma, which can be observed in the retina of the eye, is a disease that can damage the eye's optic nerve and result in vision loss and blindness. It is a cumbersome task to identify this in its early stage. As a result, it is also called the silent thief of vision. The rise in Intra Ocular Pressure (IOP) causes Glaucoma by affecting the structural changes of glaucoma.

Glaucoma is a chronic eye condition in which the nerve that connects the eye to the brain (optic nerve) is progressively damaged. Patients with early glaucoma do not have visual symptoms. Progression of the disease results in loss of peripheral vision, so patients may complain of "tunnel vision" (only being able to see the center). Advanced glaucoma is associated with total blindness. According to the World Health Organization (WHO), Glaucoma is the second leading cause of blindness around the world. In 2020, about 80 million people have glaucoma worldwide, and this number is expected to increase to over 111 million by 2040. People over 60 are at increased risk of glaucoma, warned by the National Eye Institute (NEI).

In the medical field, fundus photography is a popular method implemented for the early screening of glaucoma. Ophthalmologists clinically detect glaucoma according to certain symptoms, including high intraocular pressure, optic nerve damage, large cup-to-disc ratio, and vision loss, which are widely used as diagnostic criteria. However, manual glaucoma assessment is expensive and time-consuming for patients as professional knowledge of ophthalmology is needed for the whole process.

Conventionally, heuristic methods are utilized by the domain expertise to extract features manually from fundus images. The manual extraction of features includes energy-based features, local configuration pattern features, higher-order spectra features, and cup-to-disc ratio features, etc. However, predefined features need to be extracted artificially, which is a laborious heuristic (requiring professional knowledge) meanwhile largely dependent on experience and luck. Furthermore, even experts may omit some important hidden patterns.

In the recent past, medical studies have demonstrated that glaucoma can be detected early by measuring the cup-to-disc ratio of the optic nerve head (the ratio of the optic cup radius to the optic disc radius, referred to as the cup-to-disc ratio) by fundus imaging. With the development of artificial intelligence technology, it is possible to calculate a cup-to-disc ratio using artificial intelligence technology more precisely to realize automatic glaucoma identification.

In existing technology, an image processing technique for glaucoma detection using a cup to disc ratio is known. In the proposed image processing technique, a method to calculate the CDR automatically from non-stereographic retinal fundus photographs. To automatically extract the disc, two methods making use of an edge detection method and a variational level-set method are proposed in the study. For the cup, color component analysis and threshold level-set method are evaluated. Ellipse fitting is applied to the extracted region of interest to obtain the boundary locations of the cup. This method simultaneously detects the edges and suppresses the uneven noises from the fundus image. The accuracy of this method is 89%. However, as the depth of the cup is not considered to detect its boundary, its detection is not efficient.

In updated technology, a method of automatic glaucoma identification is described in the patent document (CN 109829877A). In the proposed method of automatic glaucoma identification, an image processing algorithm is used to preliminarily locate the optic disc in the fundus image, and a depth convolution neural network is used to segment the optic disc region and the optic cup region from the preliminarily located region, and then the cup-to-disc ratio is calculated. As a result, the estimated CDR value is used to determine the existence of glaucoma in the fundus image. However, in the above glaucoma identification method, a complex image processing algorithm is required to initially position the optic disc. The accuracy of optic disc positioning affects the accuracy of subsequent optic cup or optic disc segmentation, thereby affecting the accuracy of cup-to-disc ratio calculation.

There are one or more technical problems with the glaucoma identification methods in the prior art. Further, in the existing art, early detection of glaucoma is a cumbersome task. The techniques for automatic glaucoma identification lack extracting low-level features which might lead to information loss of features, especially edges. Further, in existing prior arts, a complex image processing algorithm is required to initially position the optic disc. The accuracy of optic disc positioning affects the accuracy of subsequent optic cup or optic disc segmentation, thereby affecting the accuracy of cup-to-disc ratio calculation. Moreover, the existing system and methods suffer computational complexity and rely on manual feature extraction techniques, and the techniques are primitive and hence, there is a fair chance of detecting false positives of the optic disc (OD) and optic cup (OC).

Therefore there is a need for a system that can detect the glaucoma disease at an early stage. There is also a need for a rapid and accurate detection system for the detection of glaucoma. There is also a need for multivariable deep learning architectures with very less false positives (FP) and false negatives (FN) results. There is also a need to reduce manual errors during faster and more reliable detection of glaucoma. Further, there is a requirement for a system that detects glaucoma at very less computational and connectivity constraints such as memory, bandwidth, and execution speed compared to existing prior arts.

SUMMARY OF THE INVENTION

In an embodiment of the present disclosure, there is provided a multivariable artificial intelligence system for early detection of glaucoma. The multivariable artificial intelligence system comprises a computing device having a control unit and one or more non-transitory storage devices for storing instructions to be executed by the control unit. The computing device is in communication with an application server via a network.

Additionally, or optionally, the computing device comprises an input module, an image enhancing module, a feature extraction module, a post image processing module, and a parameter selection module. The input module may be configured to receive at least one fundus retinal image. The image enhancing module may be configured to receive at least one fundus retinal image for preprocessing to improve the quality by reducing the effect of noise and adjusting the contrast levels. The image enhancing module comprises pre-processing techniques such as a patch-wise restoring, a contrast enhancement, a contrast adjustment, and thereof to reduce the information losses while resizing the high-resolution image to low resolution image.

Additionally, or optionally, the feature extraction module may be configured with a pair of models to segment an optic disc (OD) and an optic cup (OC) region from the preprocessed fundus retinal image. The feature extraction module may comprise a plurality of modules such as a spatial feature extractor (SFE) module, a dilated global pyramid convolution module, a channel discriminator (CD) module, and an edge extraction to extract both edge and spatial information of the fundus retinal image.

Additionally, or optionally, the pair of models may comprise a feature fusion model and an edge extraction model. The feature fusion model to extract the spatial features of the preprocessed fundus retinal image. The feature fusion model may be a multi spatial attention feature fusion (MSAFF) model. The edge extraction model may be configured to extract edge level features of the preprocessed fundus retinal image. The edge extraction model is a multi-dilated edge extraction (MDEE) model.

Additionally, or optionally, the post image processing module may be configured to receive the segmented optic disc (OD) and the optic cup (OC) region to estimate a plurality of parameters for each of the pair of models. The post image processing module may be configured to compute maximum and minimum intensity pixels to crop out the unwanted pixels from the segmented optic disc (OD) and the optic cup (OC) region. The post image processing module may be configured to enable the crop out segmented Optic Disc optic disc (OD) and the (OC) maps to focus more on the optic disc (OD) and the optic cup (OC) regions. The post image processing module may be configured to recognize boundary parameters of the optic disc (OD) and the optic cup (OC) regions to estimate the plurality of parameters by applying threshold techniques. The boundary parameters comprise boundaries of the optic disc (OD) and the optic cup (OC), vertical diameters of the OD and OC, centroid values, and thereof to evaluate the plurality of parameters in for each of the pair of models.

Additionally, or optionally, the parameter selection module may be configured to select the optimum parameters from the pair of models. The plurality of parameters comprises a vertical cup-to-disc ratio (CDR), a horizontal cup-to-disc ratio (CDR), a neuro retinal rim (NRR) area along with inferior superior nasal and temporal parameters (ISNT), and a papilledema (PPA) to detect the Glaucoma disease. The computing device may be configured to receive the best parameters from the pair of models and other clinical parameters as input for glaucoma detection and estimate the risk score of glaucoma. In addition to the plurality of parameters, along with technical parameters like CDR, NRR, ISNT, etc., other clinical parameters may include family history, an intra ocular pressure (IOP), etc.

are also considered and provided as input to Field-programmable gate array (FPGA) board to predict the presence of glaucoma. The parameter selection module selects the best parameters by calculating the cup-to-disc ratio (CDR), inferior superior nasal and temporal parameters (ISNT), and entropy parameters of the multi spatial attention feature fusion (MSAFF) model and the multi-dilated edge extraction (MDEE) model. Further, it also predicts the risk of glaucoma to the patients alerting them to take necessary precautions before going into the severe condition.

Additionally, or optionally, the optimal parameters from the pair of models from the parameter selection module are input into the control unit by using a hardware description language synthesis through a programming language. The programming language includes a Verilog programming language, a very high-speed integrated circuit hardware description language (VHDL), and thereof. The control unit is configured with at least one field-programmable gate array (FPGA) board to predict the presence of Glaucoma by analyzing the received optimal parameters from the pair of models.

In another aspect of the present disclosure, there is provided training for the multi spatial attention feature fusion (MSAFF) model and the multi-dilated edge extraction (MDEE) model. The feature extraction module and the post image processing module are in communication with the control unit. In the first step, the control unit may be configured to receive a validation dataset obtained from a plurality of data sources as the reference data. In the next step, the control unit store the reference data in a database, wherein the database is in communication with the computing device over the network. Later in the next step, the control unit receives at least one fundus retinal image from the input module.

In the next step, the control unit compares at least one fundus retinal image from the input module with the reference data from the database. In the next step, the control unit extracts spatial features and edge features by utilizing the plurality of modules such as a spatial feature extractor (SFE) module, a dilated global pyramid convolution module, and a channel discriminator (CD) module. Finally, the control unit train the feature fusion model and the edge extraction model using the input data and the reference data as training data to extract segmented optic disc (OD) and the optic disc (OC) maps from the input data, thereby accurately detecting the early stage of glaucoma. In addition, it predicts the risk of glaucoma for the patients and warns the patient to take necessary precautions before entering the severe condition.

Additionally, or optionally, the plurality of data sources comprises at least one data warehouse, at least one health care center, a plurality of outpatient and clinical visits data, discharge reports, electronic medical records, picture archiving, and communication systems. The training of the models is implemented using hyper-parameters less than 0.5M and enabling the network to extract both edge and spatial information. During the training of each model, the best accuracy, dice coefficients, and loss values & their relevant weights of both training and validation data are estimated and stored for stabilization of the network.

Yet another aspect of the present disclosure, there is provided a method for early detection of glaucoma using multivariable artificial intelligence. In the first step, at least one fundus retinal image may be received by the input module. In the next step, the image enhancing module may be configured to preprocess at least one fundus retinal image to improve the quality of at least one fundus retinal image by reducing the effect of noise and adjusting contrast levels.

Later in the next step, the feature extraction module may be configured with a pair of models to segment an optic disc (OD) and an optic cup (OC) for features mapping to extract spatial features and edge level features of the preprocessed fundus retinal image. In the next step, the post image processing module estimates the plurality of parameters for each of the pair of models. In the next step, the parameter selection module may select optimal parameters from the pair of models. In the final step, the control unit detects glaucoma by utilizing the best parameters from the pair of models and other clinical parameters.

Additionally, or optionally, the estimation of the plurality of parameters in the post image processing module may be configured to compute maximum and minimum intensity pixels to crop out the unwanted pixels from the segmented optic disc (OD) and the optic cup (OC) region. The post image processing module may be configured to focus on the optic disc (OD) and the optic cup (OC) regions. Finally, the post image processing module may be configured to recognize the boundary parameters of the optic disc (OD) and the optic cup (OC) regions to estimate the plurality of parameters by applying threshold techniques. The boundary parameters may comprise boundaries of the optic disc (OD) and the optic cup (OC), vertical diameters of the OD and OC, centroid values, and thereof to evaluate the plurality of parameters in each of the pair of models.

BRIEF DESCRIPTION OF DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein.

FIG. 3 represents a flowchart illustrating a method for early detection of glaucoma using a multivariable artificial intelligence system in accordance with yet another embodiment of the present disclosure.

DETAILED DESCRIPTION OF THE EMBODIMENTS

Figure 1:
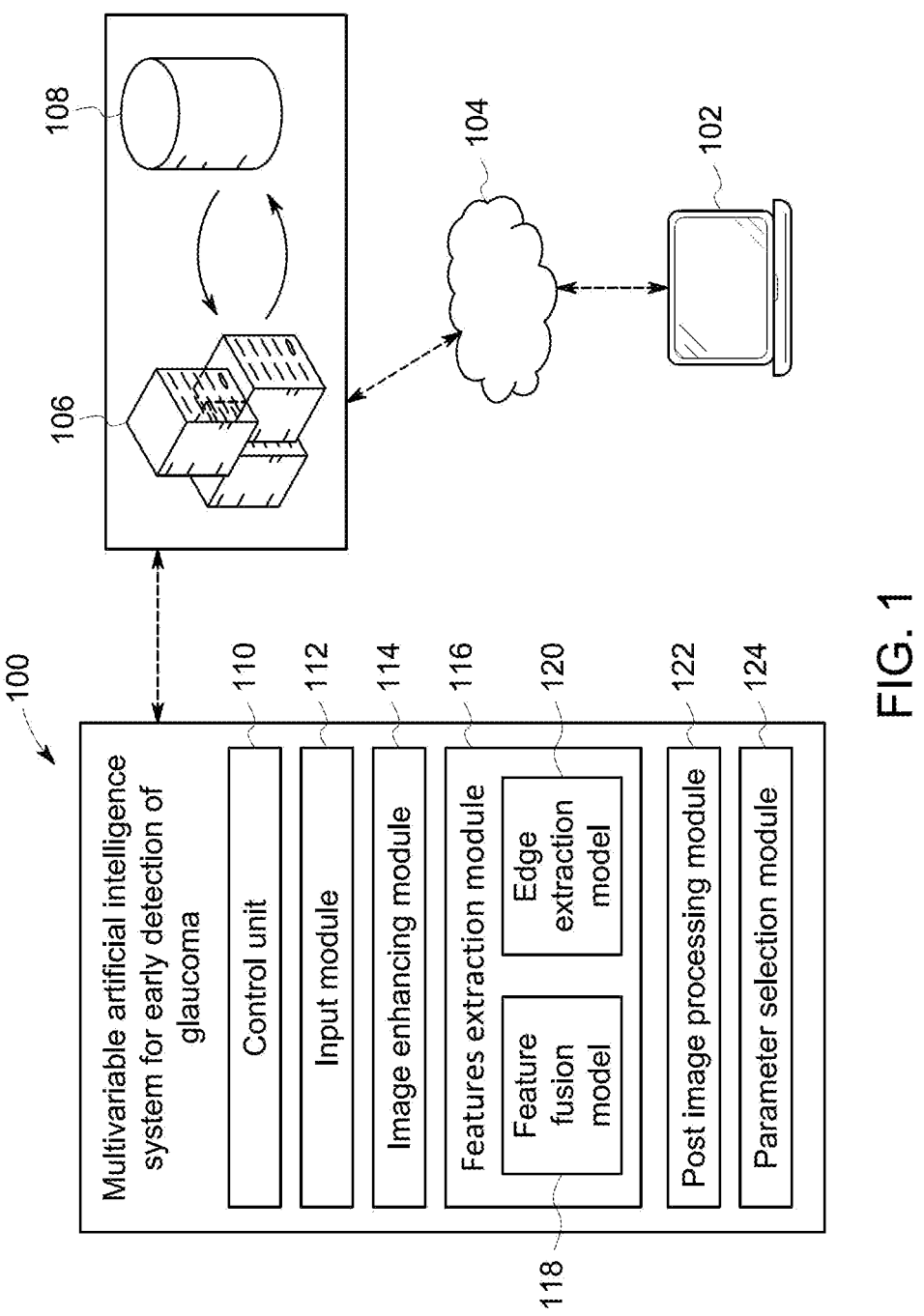
FIG. 1 is a block diagram illustrating a multivariable artificial intelligence system according to one embodiment of the present disclosure.

Example apparatus are described herein. Other example embodiments or features may further be utilized, and other changes may be made, without departing from the spirit or scope of the subject matter presented herein. In the following detailed description, reference is made to the accompanying drawings, which form a part thereof.

The example embodiments described herein are not meant to be limiting. It will be readily understood that the aspects of the present disclosure, as generally described herein, and illustrated in the drawings, can be arranged, substituted, combined, separated, and designed in a wide variety of different configurations, all of which are explicitly contemplated herein.

FIG. 1 is a block diagram illustrating a multivariable artificial intelligence system 100. The multivariable artificial intelligence system 100 comprises a computing device 102 having a control unit 110 and one or more non-transitory storage devices 108 for storing instructions to be executed by the control unit 110. The computing device 102 is in communication with an application server 106 via a network 104.

Additionally, or optionally, the computing device 102 comprises, an input module 112, an image enhancing module 114, a feature extraction module 116, a post image processing module 122, and a parameter selection module 124. The input module 112 may be configured to receive at least one fundus retinal image. The image enhancing module 114 may be configured to receive at least one fundus retinal image from the input module 112 for preprocessing to improve the quality of at least one fundus retinal image by reducing the effect of noise and adjusting contrast levels. The image enhancing module 114 comprises pre-processing techniques such as a patch-wise restoring, a contrast enhancement, a contrast adjustment, and thereof to reduce the information losses while resizing the high-resolution image to low resolution image. Each module described herein may be implemented as a set of processor-executable instructions stored in a non-transitory memory and executed by one or more processors.

Additionally, or optionally, the feature extraction module 116 may be configured with a pair of models to segment an optic disc (OD) and an optic cup (OC) region from the preprocessed fundus retinal image. The feature extraction module may comprise a plurality of modules such as a spatial feature extractor (SFE) module, a dilated global pyramid convolution module, a channel discriminator (CD) module, and an edge extraction to extract both edge and spatial information of the fundus retinal image.

Additionally, or optionally, the pair of models may comprise a feature fusion model 118 and an edge extraction model 120. The feature fusion model 118 to extracts spatial features of the preprocessed fundus retinal image. The feature fusion model 118 may be a multi spatial attention feature fusion (MSAFF) model. The edge extraction model 120 may be configured to extract edge level features of the preprocessed fundus retinal image. The edge extraction model 120 is a multi-dilated edge extraction (MDEE) model.

Additionally, or optionally, the post image processing module 122 may be configured to receive the segmented optic disc (OD) and the optic cup (OC) region to estimate a plurality of parameters for each of the pair of models (118 and 120). The post image processing module 122 may be configured to compute maximum and minimum intensity pixels to crop out the unwanted pixels from the segmented optic disc (OD) and the optic cup (OC) region. The post image processing module 122 may be configured to enable the crop out segmented optic disc (OD) and the optic cup (OC) maps to focus more on the optic disc (OD) and the optic cup (OC) regions. The post image processing module 122 may be configured to recognize boundary parameters of the optic disc (OD) and the optic cup (OC) regions to estimate the plurality of parameters by applying threshold techniques. The boundary parameters comprise boundaries of the optic disc (OD) and the optic cup (OC), vertical diameters of the OD and OC, centroid values, and thereof to evaluate the plurality of parameters for each of the pair of models.

Additionally, or optionally, the parameter selection module 124 may be configured to select the optimum parameters from the pair of models. The plurality of parameters comprises a vertical cup-to-disc ratio (CDR), a horizontal cup-to-disc ratio (CDR), a neuro retinal rim (NRR) area along with inferior, superior, nasal, and temporal parameters (ISNT), and a papilledema (PPA) to detect the Glaucoma disease. The computing device 102 may be configured to receive the best parameters from the pair of models (118 and 120) and other clinical parameters as input for glaucoma detection and predict the risk score of glaucoma. The patient can check the risk score to take necessary precautions before entering the severe condition. The other clinical parameters may include family history, an Intra Ocular Pressure (IOP), and any other parameters to detect glaucoma. The parameter selection module 124 is configured to select the optimum parameters from the pair of models (118 and 120). This selection is performed by calculating and comparing the cup-to-disc ratio (CDR), inferior superior nasal and temporal parameters (ISNT), and entropy parameters from the outputs of both the multi spatial attention feature fusion (MSAFF) model and the multi-dilated edge extraction (MDEE) model. The parameters demonstrating minimal entropy or maximum diagnostic correlation are selected as the optimum parameters for glaucoma detection. For example, when the entropy of the MDEE output is approximately 0.12 bits lower than that of the MSAFF output for the same fundus region, the processor selects the MDEE-derived CDR value as the optimum parameter. This illustrates the comparative evaluation criterion used by the system to identify diagnostically superior outputs.

Additionally, or optionally, the optimal parameters from the pair of models (118 and 120) from the parameter selection module 124 are input into the control unit 110 by using a hardware description language synthesis through a programming language. The programming language includes a verilog programming language, a very high-speed integrated circuit hardware description language (VHDL), and thereof. The control unit 110 is configured with at least one field-programmable gate array (FPGA) board to predict the presence of glaucoma by analyzing the received optimal parameters from the pair of models (118 and 120).

In another aspect of the present disclosure, there is provided training for the multi spatial attention feature fusion (MSAFF) model 118 and the multi-dilated edge extraction (MDEE) model 120. The feature extraction module 116 and the post image processing module 122 are in communication with the control unit 110. In the first step, the control unit 110 may be configured to receive a validation dataset obtained from a plurality of data sources as the reference data. In the next step, the control unit 110 stores the reference data in a database of one or more non-transitory storage devices 108, wherein the database is in communication with the computing device 102 over the network 104. Later in the next step, the control unit 110 receives the at least one fundus retinal image from the input module 112.

In the next step, the control unit 110 compare at least one fundus retinal image from the input module 112 with the reference data from the database of one or more non-transitory storage devices 108. In the next step, the control unit 110 extracts the spatial features and the edge features by utilizing the plurality of modules such as a spatial feature extractor (SFE) module, a dilated global pyramid convolution module, a channel discriminator (CD) module. Finally, the control unit 110 trains the feature fusion model 118 and the edge extraction model 120 using the input data and the reference data as training data to extract segmented optic disc (OD) and the optic cup (OC) maps from the input data, thereby accurately detecting the early stage of glaucoma.

In one embodiment herein, the plurality of data sources comprises at least one, but not limited to, a data warehouse, at least one health care center, a plurality of outpatient and clinical visits data, discharge reports, electronic medical records, picture archiving, and communication systems. The training of the models is implemented by providing a validation dataset captured from different data sources and provided in batches to the network with a batch size of 4. While training the data, for each epoch, the best accuracy, dice coefficients, and loss values & their relevant weights of both training and validation data are estimated and stored for stabilization of the network. The more effective segmentation of the optic disc (OD) and the optic cup (OC) requires the integration of multivariate feature maps that are extracted from various modules, including the spatial feature extractor (SFE) block, the dilated global pyramid convolution module, the channel discriminator (CD), etc. The entire architecture is implemented using hyper-parameters less than 0.5M and enabling the network to extract both edge and spatial information. The training of each model, the best accuracy, dice coefficients, and loss values and their relevant weights of both training and validation data are estimated and stored for stabilization of the network.

Figure 2:
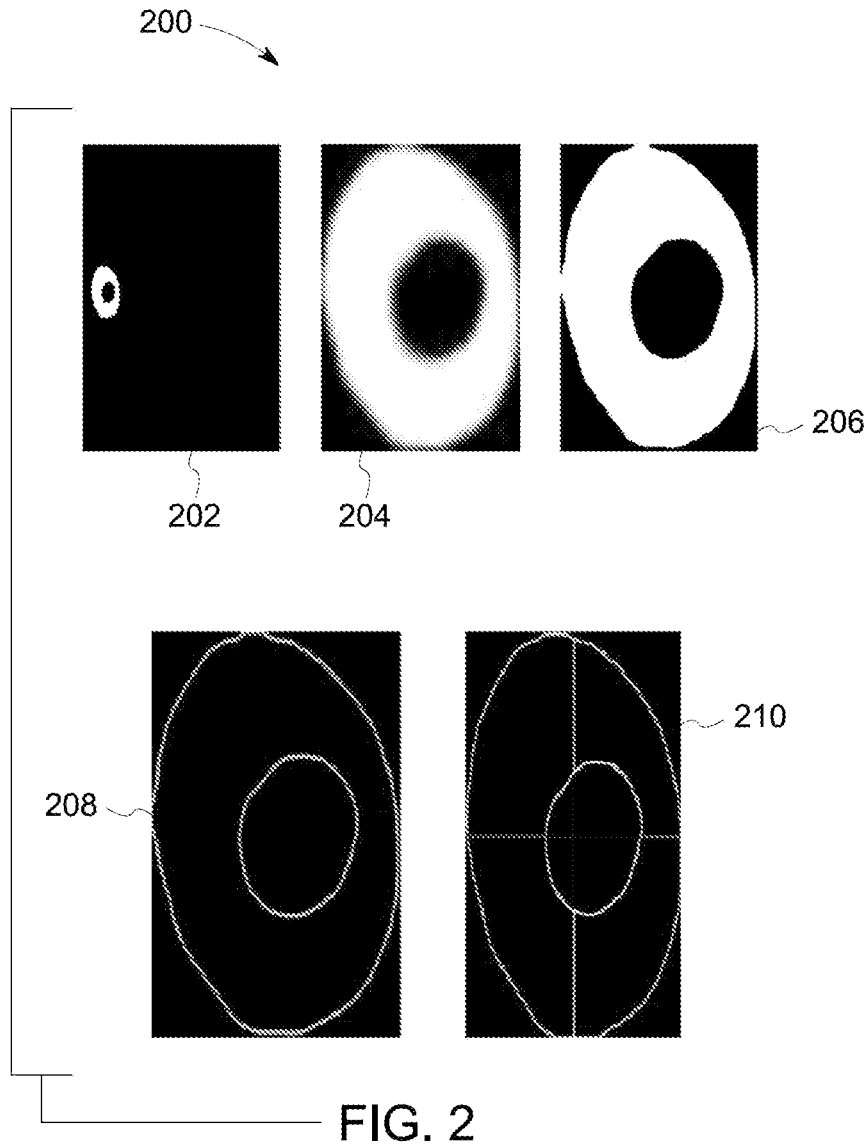
FIG. 2 illustrates post image processing images of the multivariable artificial intelligence system according to one embodiment of the present disclosure.

FIG. 2 illustrates a post image processing images 200 of the multivariable artificial intelligence system 100. The post image processing module 122 may be configured to compute maximum and minimum intensity pixels of the fundus retinal image 202. The fundus retinal image 202 may be cropped out of the unwanted pixels from the segmented optic disc (OD) and the optic cup (OC) region in FIGS. 204 and 206. The post image processing module may be configured to focus on the optic disc (OD) and the optic cup (OC) regions 208. Finally, the post image processing module may be configured to recognize the boundary parameters of the optic disc (OD) and the optic cup (OC) regions to estimate the plurality of parameters by applying threshold techniques to the fundus retinal image in FIG. 210. The boundary parameters of the optic disc (OD) and the optic cup (OC) regions may comprise boundaries of the optic disc (OD) and the optic cup (OC), vertical diameters of the OD and OC, centroid values and thereof to evaluate the plurality of parameters in for each of the pair of models.

FIG. 3 represents a flowchart illustrating a method 300 for early detection of glaucoma using multivariable artificial intelligence system 100 in accordance with yet another embodiment of the present disclosure.

At step 302, at least one fundus retinal image may be received by the input module 112. At step 304, the image enhancing module 114 may be configured to preprocess the at least one fundus retinal image to improve the quality of the image by reducing the effect of noise and adjusting contrast levels.

At step 306, the feature extraction module 116 may be configured with a pair of models (118 and 120) to segment an optic disc (OD) and an optic cup (OC) for feature mapping to extract spatial features and edge level features of the preprocessed fundus retinal image. At step 308, the post image processing module 122 estimates the plurality of parameters for each of the pair of models (118 and 120). At step 310, the parameter selection module 124 may select optimal parameters from the pair of models (118 and 120). At step 312, the control unit 110 detects glaucoma by utilizing the best parameters from the pair of models (118 and 120) and other clinical parameters.

In one embodiment herein, the estimation of the plurality of parameters in the post image processing module 122 may be configured to compute the maximum and minimum intensity pixels to crop out the unwanted pixels from the segmented optic disc (OD) and the optic cup (OC) region. The post image processing module 122 may be configured to focus on the optic disc (OD) and the optic cup (OC) regions. Finally, the post image processing module 122 may be configured to recognize the boundary parameters of the optic disc (OD) and the optic cup (OC) regions to estimate the plurality of parameters by applying threshold techniques. From these located boundaries of the optic disc (OD) and the optic cup (OC), vertical diameters of the optic disc (OD) and the optic cup (OC), centroid values are evaluated to calculate the CDR, NRR, PPA and ISNT values in for each of the pair of models (118 and 120).

Numerous advantages of the present disclosure may be apparent from the discussion above. In accordance with the present disclosure, a multivariable artificial intelligence guided hardware monitoring system for early detection of glaucoma may be implemented. The proposed multivariable artificial intelligence system provides a deep learning architecture to segment the optic disc and optic cup in two ways using two different networks termed multi spatial attention feature fusion network (MSAFF-Net) and multi-dilated edge extraction network (MDEE-Net) respectively.

The proposed multivariable artificial intelligence system can predict the risk score of glaucoma with a plurality of parameters. The system can estimate the risk score of glaucoma, which acts as an early indicator and alert the patient before going to an irreversible condition. The system reduces the number of false positives (FP) and false negatives (FN) as compared to true positives and true negatives. The multivariable artificial intelligence guided hardware monitoring system achieves an accuracy of more than 95%. The proposed multivariable artificial intelligence system provides a low-cost, rapid and accurate detection system for the detection of glaucoma disease and estimates the risk score of glaucoma.

The proposed multivariable artificial intelligence system may be faster and more reliable and reduces manual errors. The proposed multivariable artificial intelligence system has high security and data privacy of the patient to maintain confidentiality. The system provides very less computational and connectivity constraints such as memory, bandwidth, and execution speed as compared to other conventional AI models.

It is to be understood that not necessarily all objectives or advantages may be achieved in accordance with any particular embodiment described herein. Thus, for example, those skilled in the art will appreciate that certain embodiments may be configured to operate in a manner that achieves or optimizes one advantage or group of advantages as taught herein without necessarily achieving other objects or advantages as may be taught or suggested herein.

All processes described herein may be embodied in, and fully automated via, software code modules executed by a computing system that includes one or more computers or processors. The software code modules may be stored in any type of non-transitory computer-readable medium or other computer storage device. Some or all methods may be embodied in specialized computer hardware.

Many other variations other than those described herein will be apparent from this disclosure. For example, depending on the embodiment, certain actions, events, or functions of any of the algorithms described herein may be performed in different sequences, and may be added, merged, or excluded altogether (e.g., not all described actions or events are required to execute the algorithm). Moreover, in certain embodiments, operations or events are performed in parallel, for example, through multithreading, interrupt handling, or through multiple processors or processor cores, or on other parallel architectures, rather than sequentially. In addition, different tasks or processes can be performed by different machines and/or computing systems that can work together.

The various exemplary logical blocks and modules described in connection with the embodiments disclosed herein can be implemented or executed by a machine such as a processor. The processor may be a microprocessor, but alternatively, the processor may be a controller, a microcontroller, or a state machine, or a combination thereof. The processor can include an electrical circuit configured to process computer executable instructions. In another embodiment, the processor includes an application specific integrated circuit (ASIC), a field programmable gate array (FPGA), or other programmable device that performs logical operations without processing computer executable instructions. The processor can also be implemented as a combination of computing devices, e.g., a combination of a digital signal processor (DSP) and a microprocessor, a plurality of microprocessors, one or more microprocessors in conjunction with a DSP core, or any other such configuration. Although described herein primarily with respect to digital technology, the processor may also include primarily analog components. For example, some or all of the signal processing algorithms described herein may be implemented by analog circuitry or mixed analog and digital circuitry. A computing environment may include any type of computer system, including, but not limited to, a computer system that is based on a microprocessor, mainframe computer, a digital signal processor, a portable computing device, a device controller, or a computing engine within the device.

Unless otherwise stated, conditional languages such as "can," "could," "will," "might," or "may" are understood within the context as used in general to convey that certain embodiments include, while other embodiments do not include, certain features, elements and/or steps. Thus, such conditional languages are not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive languages, such as the phrase "at least one of: X, Y, or Z," unless specifically stated otherwise, is understood with the context as used in general to present that an item, term, etc., may be either X, Y, or Z, or any combination thereof (e.g., X, Y, and/or Z). Thus, such a disjunctive language is not generally intended to, and should not, imply that certain embodiments require at least one of: X, at least one of Y, or at least one of: Z to each be present.

Any process descriptions, elements, or blocks in the flow diagrams described herein and/or shown in the accompanying drawings should be understood as potentially representing modules, segments, or parts of code, including one or more executable instructions for implementing a particular logical function or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

For example, "a processor configured to carry out recitations A, B and C" can include a first processor configured to carry out recitation A working in conjunction with a second processor configured to carry out recitations B and C. The same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

For expository purposes, the term "horizontal" as used herein is defined as a plane parallel to the plane or surface of the floor of the area in which the system being described is used or the method being described is performed, regardless of its orientation. The term "floor" can be interchanged with the term "ground" or "water surface". The term "vertical" refers to a direction perpendicular to the horizontal as just defined. Terms such as "above," "below," "bottom," "top," "side," "higher," "lower," "upper," "over," and "under" are defined with respect to the horizontal plane.

As used herein, the terms "attached," "connected," "coupled," and other such relational terms should be construed, unless otherwise noted, to include removable, moveable, fixed, adjustable, and/or releasable connections or attachments. The connections/attachments can include direct connections and/or connections having intermediate structure between the two components discussed.

Numbers preceded by a term such as "approximately," "about," and "substantially" as used herein include the recited numbers, and also represent an amount close to the stated amount that still performs a desired function or achieves a desired result. For example, the terms "approximately," "about," and "substantially" may refer to an amount that is within less than 10% of the stated amount. Features of embodiments disclosed herein preceded by a term such as "approximately," "about," and "substantially" as used herein represent the feature with some variability that still performs a desired function or achieves a desired result for that feature.

It should be emphasized that many variations and modifications may be made to the above-described embodiments, the elements of which are to be understood as being among other acceptable examples. All such modifications and variations are intended to be included herein within the scope of this disclosure and protected by the following claims.

We claim:

1. A multivariable artificial intelligence (AI) based monitoring system for detecting glaucoma, comprising:
   a processor operatively coupled to one or more non-transitory storage devices storing executable instructions,
   wherein the processor is configured to execute instructions for:
   receiving at least one retinal fundus image of an eye;
   preprocessing the received retinal fundus image for enhancing the quality of the at least one retinal fundus image by reducing an effect of noise and adjusting contrast levels;
   segmenting, from the preprocessed retinal fundus image,
   a first set of optic disc (OD) and optic cup (OC) segmentation maps using a feature fusion model, and
   a second set of optic disc (OD) and optic cup (OC) segmentation maps using an edge extraction model;
   extracting contours from each of the first set and the second set of segmentation maps and determining boundary parameters;
   determining a plurality of diagnostic parameters for each of the first set and the second set of segmentation maps based on the boundary parameters;
   selecting a first set of selected diagnostic parameters comprising a cup-to-disc ratio (CDR) value, an inferior-superior-nasal-temporal (ISNT) value, and an entropy value from the plurality of diagnostic parameters corresponding to the first set of segmentation maps, and selecting a second set of selected diagnostic parameters comprising a CDR value, an ISNT value, and an entropy value from the plurality of diagnostic parameters corresponding to the second set of segmentation maps; and
   detecting glaucoma by analyzing the selected diagnostic parameters in combination with patient-specific clinical data.

2. The multivariable artificial intelligence system of claim 1, wherein the processor is configured to pre-process the retinal fundus image by performing patch-wise restoring, contrast enhancement and contrast adjustment to reduce the information losses while resizing the high-resolution image to low resolution image.

3. The multivariable artificial intelligence system of claim 1, wherein the feature fusion model is a multi spatial attention feature fusion (MSAFF) Network model and the edge extraction model is a multi-dilated edge extraction net (MDEE) model.

4. The multivariable artificial intelligence system of claim 1, wherein the processor is configured to: crop out unwanted portions and extract contours from the segmented optic disc (OD) and the optic cup (OC) maps for determining the boundary parameters including vertical diameters and centroid values in order to determine cup-to-disc ratio (CDR) values, neuro retinal rim (NRR) values, papilledema (PPA) values, and inferior, superior, nasal, and temporal parameters (ISNT) values.

5. The multivariable artificial intelligence system of claim 1, wherein the processor is configured with a field-programmable gate array (FPGA) to execute one or more functions for analyzing the selected diagnostic parameters, obtained from the first set and the second set of segmentation maps generated by the feature fusion model and the edge extraction model, respectively, in combination with patient-specific clinical data, to detect glaucoma and generate a glaucoma risk score.

6. The multivariable artificial intelligence system of claim 1, wherein the one or more selected diagnostic parameters from the feature fusion model and the edge extraction model are provided as an input to the processor using a hardware description language synthesis through a programming language.

7. The multivariable artificial intelligence system of claim 6, wherein the programming language includes at least any one of a verilog programming language, and a very high-speed integrated circuit hardware description language (VHDL).

8. The multivariable artificial intelligence system of claim 1, wherein the processor is configured to:
   receive a validation dataset obtained from a plurality of data sources as reference data;

store the reference data in a database, wherein the database is in communication with the computing device over a network;

receive the at least one retinal fundus image of an eye as input data;

compare reference data received from database with the input data;

extract the spatial features and the edge features from the input data using the feature fusion model and the edge extraction model; and train the feature fusion model and the edge extraction model using the input data and the reference data as training data to extract the spatial features and the edge features from the input data, thereby detecting glaucoma.

9. The multivariable artificial intelligence system of claim 8, wherein the plurality of data sources comprises data warehouses, health care centers, outpatient and clinical visits data, discharge reports, electronic medical records, picture archiving, and communication systems.

10. The multivariable artificial intelligence system of claim 1, wherein the feature fusion model and the edge extraction model are implemented using hyper-parameters less than 0.5M.

11. A method for detecting glaucoma using a multivariable artificial intelligence (AI) based monitoring system, comprising:

receiving, by a processor, at least one retinal fundus image of an eye;

preprocessing, by the processor, the at least one retinal fundus image for enhancing the quality of the at least one retinal fundus image by reducing the effect of noise and adjusting contrast levels;

segmenting, by the processor, a first set of optic disc (OD) and optic cup (OC) segmentation maps using a feature fusion model, and a second set of optic disc (OD) and optic cup (OC) segmentation maps using an edge extraction model;

extracting, by the processor, contours from each of the first set and the second set of segmentation maps and determining boundary parameters;

determining, by the processor, a plurality of diagnostic parameters for each of the first set and the second set of segmentation maps based on the boundary parameters;

selecting a first set of selected diagnostic parameters comprising a cup-to-disc ratio (CDR) value, an inferior-superior-nasal-temporal (ISNT) value, and an entropy value from the plurality of diagnostic parameters corresponding to the first set of segmentation maps, and selecting a second set of selected diagnostic parameters comprising a cup-to-disc ratio (CDR) value, an inferior-superior-nasal-temporal (ISNT) value, and an entropy value from the plurality of diagnostic parameters corresponding to the second set of segmentation maps; and detecting, by the processor, glaucoma by analyzing the selected diagnostic parameters in combination with patient-specific clinical data.

12. The method for detecting glaucoma using the multivariable artificial intelligence (AI) based monitoring system of claim 11, wherein determining the plurality of diagnostic parameters by the processor, comprises:

cropping out unwanted portions and extracting contours from the segmented optic disc (OD) and the optic cup (OC) maps; and determining boundary parameters including vertical diameters and centroid values to determine cup-to-disc ratio (CDR) values, neuro retinal rim (NRR) values, papilledema (PPA) values, and inferior superior nasal and temporal parameters (ISNT) values.

13. The method for detecting glaucoma using the multivariable artificial intelligence (AI) based monitoring system of claim 11, wherein the feature fusion model is a multi spatial attention feature fusion (MSAFF) network model, and the edge extraction model is a multi-dilated edge extraction net (MDEE) model.

* * * * *